United States Patent
Kutschera et al.

(10) Patent No.: US 7,476,772 B2
(45) Date of Patent: Jan. 13, 2009

(54) PROCESS FOR PREPARING CHLORINATED CARBONYL COMPOUNDS IN JET LOOP REACTORS

(75) Inventors: Dirk Kutschera, Neuoetting (DE);
Franz-Xaver Riener, Kirchdorf (DE);
Michael Schlueter, Ottersberg (DE)

(73) Assignee: Wacker Chemie AG, Munich (DE)

( * ) Notice: Subject to any disclaimer, the term of this patent is extended or adjusted under 35 U.S.C. 154(b) by 0 days.

(21) Appl. No.: 11/938,814

(22) Filed: Nov. 13, 2007

(65) Prior Publication Data

US 2008/0114196 A1   May 15, 2008

(30) Foreign Application Priority Data

Nov. 13, 2006  (DE) .................. 10 2006 053 380

(51) Int. Cl.
*C07C 17/00* (2006.01)
*C07C 45/00* (2006.01)
(52) U.S. Cl. ..................... 570/217; 568/348
(58) Field of Classification Search ........... 570/217; 568/348
See application file for complete search history.

(56) References Cited

U.S. PATENT DOCUMENTS

2003/0028046 A1* 2/2003 Stamm et al. .............. 558/440
2004/0013595 A1* 1/2004 Kwon et al. ................ 423/406

FOREIGN PATENT DOCUMENTS

| DE | 198 42 332 A1 | 3/2000 |
| DE | 100 10 594 A1 | 9/2001 |
| DE | 102 23 649 C1 | 8/2003 |
| EP | 0 234 503 A2 | 9/1987 |
| EP | 0 396 168 A1 | 11/1990 |
| GB | 2 036 016 A | 6/1980 |

OTHER PUBLICATIONS

Van Dierendonck et al., Loop Venturi Reactor—A Feasible Alternative to Stirred Tank Reactors?, Ind. Eng. Chem. Res., 1998, pp. 734-738, vol. 37.

* cited by examiner

*Primary Examiner*—Jafar Parsa
(74) *Attorney, Agent, or Firm*—Brooks Kushman P.C.

(57) ABSTRACT

The present invention relates to a process for preparing chlorinated or partly chlorinated carbonyl compounds, which comprises reacting unchlorinated or partly chlorinated carbonyl compounds with a chlorinating agent in a jet loop reactor.

20 Claims, 5 Drawing Sheets

Jet zone loop reactor (JZR) with partial recycling

1  Jet zone
2  Reaction zone
3  Inserted tube
4  Impingement plate
5  Two-substance nozzle
6  Bottom valve
7  Reflux valve
8  Circulation pump
9  Carbonyl compound, partly chlorinated carbonyl compound feed
10 Chlorine feed
11 Offgas
12 Product outlet
13 Ring space Fig. 1: Jet zone loop reactor (JZR) with partial recycling 1 Jet zone
2 Reaction zone
3 Inserted tube
4 Impingement plate
5 Two-substance nozzle
6 Bottom valve
7 Reflux valve
8 Circulation pump
9 Carbonyl compound, partly chlorinated carbonyl compound feed
10 Chlorine feed
11 Offgas
12 Product outlet
13 Ring space

Fig. 2: Jet zone reactor (JZR) without partial recycling

1 Jet zone
2 Reaction zone
3 Inserted tube
4 Impingement plate
5 Two-substance nozzle
6 Chlorine feed
7 Carbonyl compound, partly chlorinated carbonyl compound feed
8 Offgas
9 Product outlet
10 Ring space

Fig. 3: Jet loop reactor (JLR) with partial recycling

1 Jet zone
2 Inserted tube
3 Impingement plate
4 Bottom valve
5 Reflux valve
6 Circulation pump
7 Carbonyl compound, partly chlorinated carbonyl compound feed
8 Chlorine feed
9 Two-substance nozzle
10 Offgas
11 Product outlet
12 Ring space

Fig. 4: Jet loop reactor (JLR) with partial recycling and solvent feed

1  Jet zone
2  Inserted tube
3  Impingement plate
4  Bottom valve
5  Reflux valve
6  Circulation pump
7  Carbonyl compound, partly chlorinated carbonyl compound feed
8  Chlorine feed
9  Two-substance nozzle
10 Offgas
11 Product outlet
12 Ring space
13 Solvent feed Fig. 5: Jet loop reactor (JLR) without partial recycling 1 Jet zone
2 Inserted tube
3 Impingement plate
4 Chlorine feed
5 Carbonyl compound, partly chlorinated carbonyl compound feed
6 Two-substance nozzle
7 Offgas
8 Product outlet
9 Ring space

PROCESS FOR PREPARING CHLORINATED CARBONYL COMPOUNDS IN JET LOOP REACTORS

BACKGROUND OF THE INVENTION

1. Field of the Invention

The present invention relates to a process for preparing chlorinated carbonyl compounds with improved selectivity and improved conversion in jet loop reactors, wherein the corresponding unchlorinated or partly chlorinated carbonyl compounds are reacted with chlorine in a continuous or semi-continuous mode.

2. Background Art

Chlorinated carbonyl compounds are building blocks for numerous products in synthetic organic chemistry for applications, for example, in the pharmaceutical and agrochemical industry.

The literature describes various methods of chlorinating carbonyl compounds. The chlorination is performed in a stirred tank, tubular reactor, a combination of tubular reactor and stirred tank, or in a bubble column. The insufficient mixing in the individual reactor types often results, locally, in an inhomogeneous chlorine concentration and in temperature inhomogeneities within the reactor, which give rise to a broad spectrum of by-products. This results in an inadequate selectivity and an inadequate conversion based on the target product.

The individual reactor types known from the prior art have substantially been optimized with regard to their mixing performance. In addition to the use of sparging stirrers in stirred tanks and static mixers in tubular reactors, a wide variety of different gas distributors are used in bubble columns, or complicated chlorinations are performed in the gas phase. The heat is removed by internal heat exchangers and optionally by external heat exchangers.

In the chlorination of carbonyl compounds, the conversions are often incomplete; selectivities and hence yields are often low. The subsequent workup, which is necessary as a result, is technically complicated, gives rise to residual substances and makes the production more expensive as a result. In addition, the chlorinated and partly chlorinated carbonyl compounds are often thermally unstable and tend to thermal decomposition.

In order to enhance the selectivities and the conversions in the chlorination reaction, the prior art has proposed various processes. EP 0234503 describes, for example, the addition of catalysts to the reaction mixture. When catalysts are used, the purity of the unchlorinated or partly chlorinated carbonyl compounds, which is relevant for high catalyst activity, is often achievable only by additional workup steps, and the high catalyst cost is reflected in the preparation costs.

GB 2036016 describes the performance of the chlorination in the gas phase. These processes are technically very complicated, since some of them require high reaction temperatures at the start for the chlorination in the gas phase, and only a low space-time yield is achieved as a result of the gas phase reaction. Multistage workup processes are likewise needed for the reactants and products, which in turn entails yield losses.

DE 19842332 discloses a jet loop reactor and a process and apparatus for biologically purifying wastewater. There is no indication that such an apparatus could be used for chlorinating compounds.

SUMMARY OF THE INVENTION

It is an object of the present invention to provide a process for preparing chlorinated or partly chlorinated carbonyl compounds, which overcomes the disadvantages of the prior art, and provides an inexpensive process with high selectivity and product purity. The invention provides a process for preparing chlorinated or partly chlorinated carbonyl compounds, which comprises reacting unchlorinated or partly chlorinated carbonyl compounds with a chlorinating agent in a jet loop reactor. These and other objects are surprisingly achieved through the use of a jet loop reactor.

DETAILED DESCRIPTION OF THE PREFERRED EMBODIMENT(S)

The principle and the construction of jet loop reactors is described in summary in the literature (Zehner, P.: Bubble Columns 4. Jet Loop Reactors, Ullmann's Encyclopedia of Industrial Chemistry, Article Online Posting Date 15 Jun. 2000). A distinction is drawn between mammoth loop reactors (airlift reactors), propeller loop reactors, and jet loop reactors.

In jet loop reactors, which include compact jet loop reactors, impingement jet loop reactors and motive jet loop reactors, the liquid and the gas are conveyed into the reactor from the top or bottom through a nozzle, which leads not only to circulation of the mixture and hence to loop formation but also to a dispersion of the gas phase.

In this type of motive jet reactors, a high energy input is needed at high gas loadings in order to ensure dispersion of the gas phase and the circulation of the mixture. By virtue of the jet zone loop reactor, the energy demand can be reduced, since dispersion and mixture circulation are separated.

A significant advantage of jet loop reactors in the chlorination reaction over bubble column reactors and other gas-liquid reactors used to date is the more intensive and rapid liquid mixing at high circulation flow and hence elevated heat and mass transfer. A further advantage arises in jet-driven loop reactors (jet loop reactor=JLR) through a finer dispersion of the gas phase and hence a greater specific phase interface. Preference is given to performing the inventive reaction in a jet zone loop reactor.

The process according to the invention enables the preparation of chlorinated or partly chlorinated carbonyl compounds with high selectivities and conversions without technically complicated process steps. In this connection, chlorinated carbonyl compounds are understood to mean those in which, aside from the carbonyl compound, all hydrogen atoms have been substituted by chlorine. Partly chlorinated carbonyl compounds are those in which, aside from the carbonyl compound, at least one hydrogen atom has been substituted by chlorine.

For the chlorination, it is possible to use one or more chlorinating agents from among chlorine, sulfuryl chloride and thionyl chloride. The chlorinating agent used is more preferably chlorine. The usable unchlorinated or partly chlorinated carbonyl compounds may be straight-chain, branched or have a cyclic structure.

The carbonyl group is attached to two carbon-containing radicals $R^1$ and $R^2$ by carbon-carbon bonds, or one of $R^1$ or $R^2$ may be hydrogen. The groups $R^1$ and $R^2$ may also comprise a ring structure and may contain heteroatoms such as nitrogen. The $R^1$ and $R^2$ radicals on the carbon atom of the carbonyl group may be the same or different. It is unimportant whether the radicals already bear one or more halogen atoms or not. Partly chlorinated compounds are those compounds in which, aside from the carbonyl compound, at least one hydrogen atom has been substituted by chlorine. The groups listed in the next paragraph may therefore also bear one or more chlorine atoms instead of the hydrogen atoms specified there, where this is chemically possible.

Examples of carbonyl compounds which can be used in the process according to the invention are ketones where $R^1$ and $R^2$ may be the same or different and are selected from the group comprising —$CH_3$ and —$(CH_2)_n$—$CH_3$; cycloketones where $R^1$ and $R^2$ are the same and are comprised of —$(CH_2)$- groups; aldehydes where $R^1$ is a hydrogen atom and $R^2$ is defined as —$(CH_2)_n$—$CH_3$; 1,3-dicarboxylic acids where $R^1$ is —O—$CH_2$—$CH_3$ and $R^2$ is —$CH_2$—CO—O—$CH_2$—$CH_3$; β-dicarbonyl compounds where $R^1$ is —$(CH_2)_n$—$CH_3$ and $R^2$ is selected from the group comprising —$CH_2$—CO—$CH_3$, —$CH_2$—CO—O—$(CH_2)_n$—$CH_3$ and —$CH_2$—CO—N—R'—R'' where R' may be H, $CH_3$, $(CH_2)_n$, and R'' may be H, $CH_3$, and $(CH_2)_n$.

Preferred compounds are monochloroacetone for ketones, cyclopentanone for cycloketones, propionaldehyde for aldehydes, diethylmalonic acid for 1,3-dicarboxylic acids, and acetylacetone, 2-acetoacetamide and ethyl acetoacetate for β-dicarbonyl compounds.

The chlorine addition can take place under standard or elevated pressure; preference being given to working at standard pressure. The reaction may take place in a continuous or semicontinuous mode. A continuous chlorine addition can also be effected with recycling of unconverted chlorine into the loop.

The chlorinating agent is metered into the unchlorinated or partly chlorinated carbonyl compound in the reactor in a volume flow ratio of from 1:1 to 1:4000, preferably from 1:30 to 1:2000. The metered addition is effected via a single-component or multicomponent mixing nozzle.

The reaction in the jet loop reactor can be performed at temperatures of –20° C. to 160° C., preferably at 5° C. to 100° C.

The unchlorinated or partly chlorinated carbonyl compounds may be present neat or in the presence of a solvent. The solvents used may be any solvent suitable for the carbonyl compound and the chlorinating agent.

Optionally, the reaction can be performed in the presence of a catalyst. The catalysts may be any catalysts suitable for use in chlorination reactions.

Figure 1:
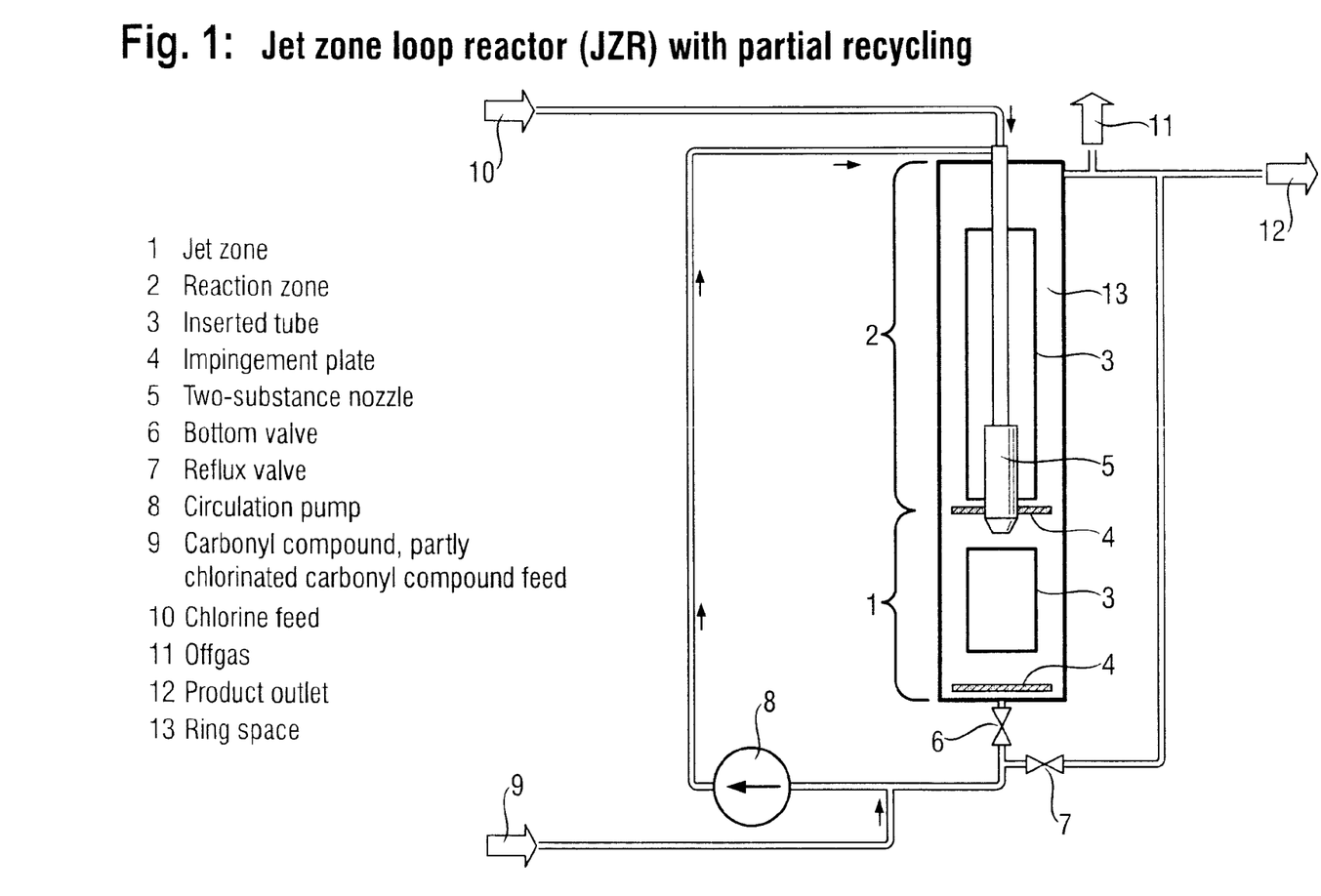
FIG. 1 shows the schematic depiction of a jet zone loop reactor (JZR) with partial recycling.

The functioning of the jet loop reactors will be illustrated by way of example using the jet zone loop reactor disclosed in DE-198 42 332 (incorporated herein by reference), particularly with regard to FIG. 1, a jet zone loop reactor (JZR) with partial recycling.

The jet zone loop reactor is divided into two different regions. Below the upper impingement plate 4 is disposed a so-called jet zone 1. This region can be considered as a compact reactor with low height-diameter ratio. The circulation pump 8 generates a free jet through the two-substance nozzle 5. Via the chlorine feed 10, the gas phase is dispersed finely at the two-substance nozzle 5 and in the free jet. The gas/liquid mixture is driven through the lower inserted tube 3 up to the lower impingement plate 4 of the reactor. At the lower impingement plate 4, the mixture is deflected, which is accompanied by a rise in the ring space 13 of the jet zone 1. The free jet of the two-substance nozzle 5 sucks a portion of the liquid back into the inserted tube 3, which leads to the formation of a loop flow. The portion of the mixture which is not sucked in flows past the upper impingement plate 4 into the reaction zone 2. Since a higher gas content is established in the ring space than in the inserted tube, there is a density difference which causes backflow. As a result of this effect, a loop forms by the airlift principle. The product can be withdrawn via the product outlet 12. Product recycling to the two-substance nozzle 5 is possible via the reflux valve 7 or via a withdrawal from the jet zone 1 through the bottom valve 6.

Owing to the controllable parameters for the reaction and reproducible process conditions, these chlorinated or partly chlorinated carbonyl compounds prepared by the process according to the invention have high selectivities and make a subsequent isolation of the product simpler or superfluous. Fractional distillation is the most frequently employed isolation method.

The invention will be illustrated in detail hereinafter with reference to examples. The examples reflect the general field of use of the present invention and should not be interpreted as restrictive. Unless stated otherwise, percentages should be understood to mean percentages by mass.

EXAMPLE 1

Semicontinuous chlorination of monochloroacetone with chlorine to 1,1,3-trichloroacetone by the inventive process in a jet zone loop reactor with partial recycling (see FIG. 1).

The selectivity for 1,1,3-trichloroacetone is defined as follows:

$$Se(1.1.3-TCA) = \frac{1.1.3-TCA}{1.1.3-TCA + 1.3-DCA + 1.1-DCA + 1.1.1-TCA + 1.1.3.3-TeCA + 1.1.1.3-TeCA}$$

TCA=trichloroacetone
DCA=dichloroacetone
TeCA=tetrachloroacetone

| | |
|---|---|
| Temperature: | 40° C. |
| Pressure: | Standard pressure |
| $Cl_2$ volume flow: | 4-5 [m³ (STP)/h] |
| Reaction time: | 10 h |
| Amount used: | 150 kg of monochloroacetone |
| Conversion after 10 h (GC): | 99% |
| Selectivity after 10 h: | 35% 1,1,3-TCA |

Procedure:

Monochloroacetone is initially charged to the reaction system via feed 9 and heated to 40° C. By virtue of the opening of the bottom valve 6 and starting circulation pump 8, a free jet is generated through the two-substance nozzle 5. The chlorine is introduced via feed 10 into the jet zone loop reactor via the two-substance nozzle 5. The temperature is kept at 40° C. by means of an external circulation cooler during the metered addition of chlorine. The conversion and the selectivity are monitored by gas chromatography. As a result of the selectivity achieved, it is possible to dispense with the addition of iodine as a catalyst. The product is isolated by means of a purifying distillation.

EXAMPLE 2

Continuous chlorination of monochloroacetone with chlorine to 1,1,3-trichloroacetone by the process the invention in a jet zone loop reactor with partial recycling. The selectivity for 1,1,3-trichloroacetone is defined as follows:

$$Se(1.1.3-TCA) = \frac{1.1.3-TCA}{1.1.3-TCA+1.3-DCA+1.1-DCA+1.1.1-TCA+1.1.3.3-TeCA+1.1.1.3-TeCA}$$

| | |
|---|---|
| Temperature: | 40° C. |
| Pressure: | Standard pressure |
| Cl$_2$ volume flow: | 4-5 [m$^3$ (STP)/h] |
| Monochloroacetone volume flow: | 15-20 [m$^3$ (STP)/h] |
| Reaction time: | 10 h |
| Conversion (GC): | 99% |
| Selectivity after 10 h: | 35% 1,1,3-TCA |

Procedure:

After monochloroacetone has been semicontinuously chlorinated with chlorine according to example 1 and the circulation pump 8 has been switched on through the bottom valve 6, monochloroacetone via feed 9 and chlorine via feed 10 are introduced continuously via the two-substance nozzle 5. The temperature is kept at a constant 40° C. by means of an external circulation cooler. The finished product is obtained continuously via the outlet 12. The conversion and the selectivity are monitored by gas chromatography. As a result of the selectivity achieved, it is possible to dispense with iodine addition as a catalyst. The product is isolated by means of a purifying distillation.

EXAMPLE 3

Semicontinuous chlorination of diethyl malonate with chlorine to diethyl chloromalonate by the process of the invention in a jet zone loop reactor with partial recycling (see FIG. 1).

The selectivity for diethyl chloromalonate (DECM) is defined as follows:

$$Se(DECM) = \frac{DECM}{DECM + DEDCM}$$

DECM=diethyl chloromalonate
DEDCM=diethyl dichloromalonate

| | |
|---|---|
| Temperature: | 50° C. |
| Pressure: | Standard pressure |
| Cl$_2$ volume flow: | 4-5 [m$^3$ (STP)/h] |
| Reaction time: | 10 h |
| Amount used: | 160 kg of diethyl malonate |
| Conversion after 10 h (GC): | 99% |
| Selectivity after 10 h: | 98% DECM |

Procedure:

Analogous to example 1, diethyl malonate is initially charged in the reaction system and heated to 50° C. After the circulation pump has been started, chlorine is introduced into the jet zone loop reactor via the metering nozzle. The temperature is kept at 50° C. by means of an external circulation cooler during the metered addition of chlorine. The conversion and the selectivity are monitored by gas chromatography. A subsequent product isolation can be dispensed with owing to the selectivity achieved.

EXAMPLE 4

Figure 2:
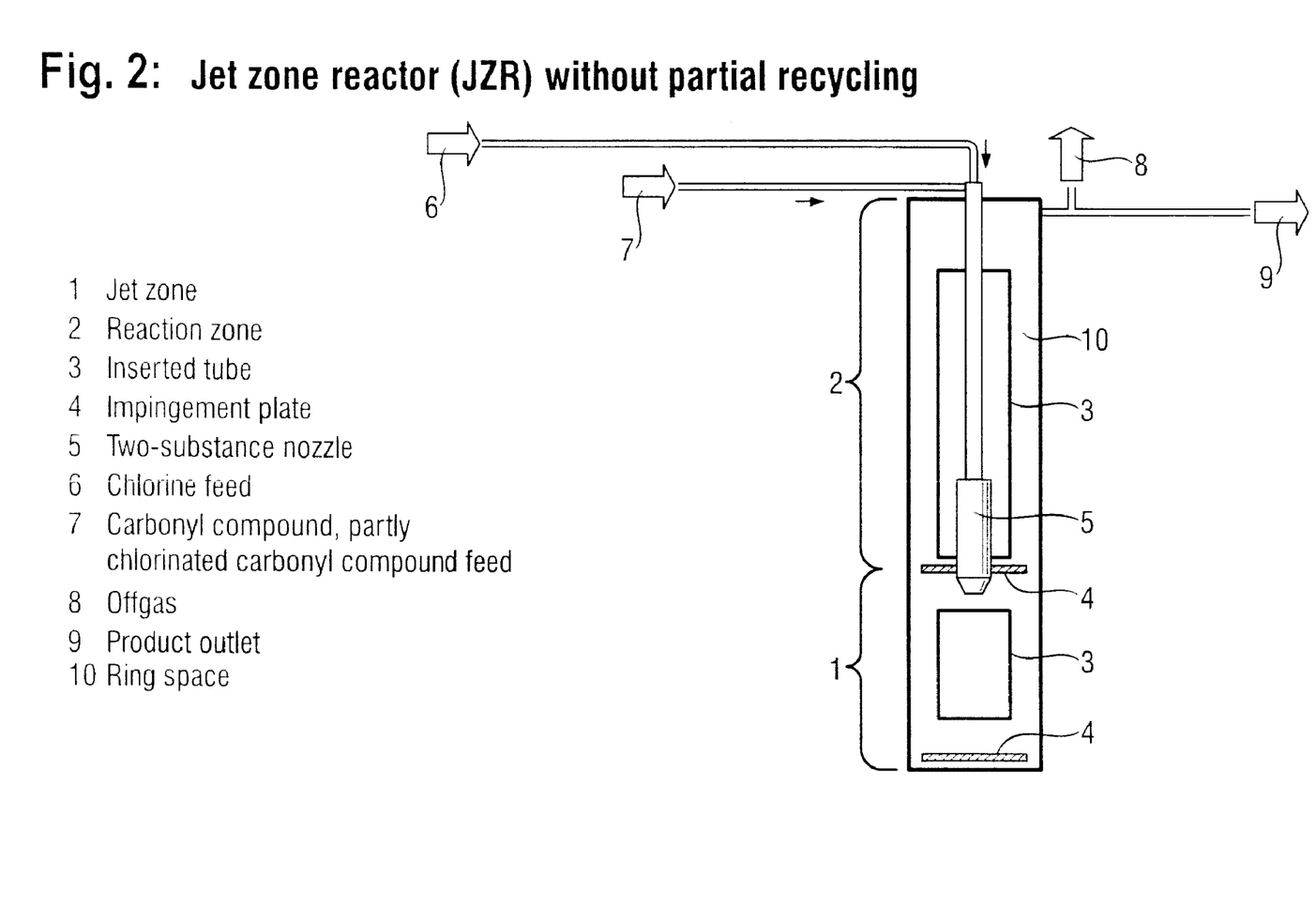
FIG. 2 shows the schematic depiction of a jet zone loop reactor (JZR) without partial recycling.

Continuous chlorination of ethyl acetoacetate with chlorine to ethyl 2-chloroacetoacetate by the process of the invention in a jet zone loop reactor without partial recycling (see FIG. 2).

The selectivity for ethyl 2-chloroacetoacetate is defined as follows:

$$Se(2\text{-}Cl\text{-}ACE) = \frac{2-ClACE}{2-ClACE+2.4-DClACE}$$

2-Cl-ACE=ethyl 2-chloroacetoacetate
2,4-DClACE=ethyl 2,4-dichloroacetoacetate

| | |
|---|---|
| Temperature: | 35° C. |
| Pressure: | Standard pressure |
| Cl$_2$ volume flow: | 40-45 [m$^3$ (STP)/h] |
| Reaction time: | 10 h |
| Ethyl acetoacetate mass flow: | 1800-2000 [kg/h] |
| Conversion after 10 h (GC): | 10% |
| Selectivity after 10 h: | 96.5% 2-Cl-ACE |

Procedure:

Ethyl acetoacetate is conveyed continuously through feed 7 into the jet zone loop reactor via the two-substance nozzle 5. After the free jet has been formed in the jet zone 2, chlorine is introduced continuously via feed 6 and two-substance nozzle 5 into the jet zone loop reactor. The temperature is kept at 35° C. by precooled ethyl acetoacetate. The finished product is obtained continuously through outlet 9. For further isolation, the excess ethyl acetoacetate is distilled out of the reaction mixture and recycled to the chlorination. The conversion and the selectivity are monitored by gas chromatography.

EXAMPLE 5

Continuous chlorination of 2-acetoacetamide with chlorine to chloroacetoacetamide by the process of the invention in a jet zone loop reactor without partial recycling (see FIG. 2).

The selectivity for chloroacetoacetamide is defined as follows:

$$Se(CAA) = \frac{CAA}{CAA + DCAA}$$

CAA=chloroacetoacetamide
DCAA=dichloroacetoacetamide

| | |
|---|---|
| Temperature: | −5° C. |
| Pressure: | Standard pressure |
| Cl$_2$ volume flow: | 20-30 [m$^3$ (STP)/h] |
| Reaction time: | 1 h |
| Ethyl acetoacetate volume flow: | 125 [m$^3$ (STP)/h] |
| Conversion after 1 h (GC): | 99% |
| Selectivity after 1 h: | 98.5% CAA |

Procedure:

Analogously to example 4, acetoacetamide is conveyed through the two-substance nozzle into the jet zone loop reactor. After the free jet has been formed in the jet zone, chlorine is introduced continuously into the jet zone loop reactor through the two-substance nozzle. The temperature is kept at −5° C. by precooled acetoacetamide and by means of jacket cooling. The target product precipitates out as a solid and is obtained continuously via the outlet. For further isolation, the solid is removed by means of a centrifuge. The conversion and the selectivity are monitored by gas chromatography.

EXAMPLE 6

Figure 4:
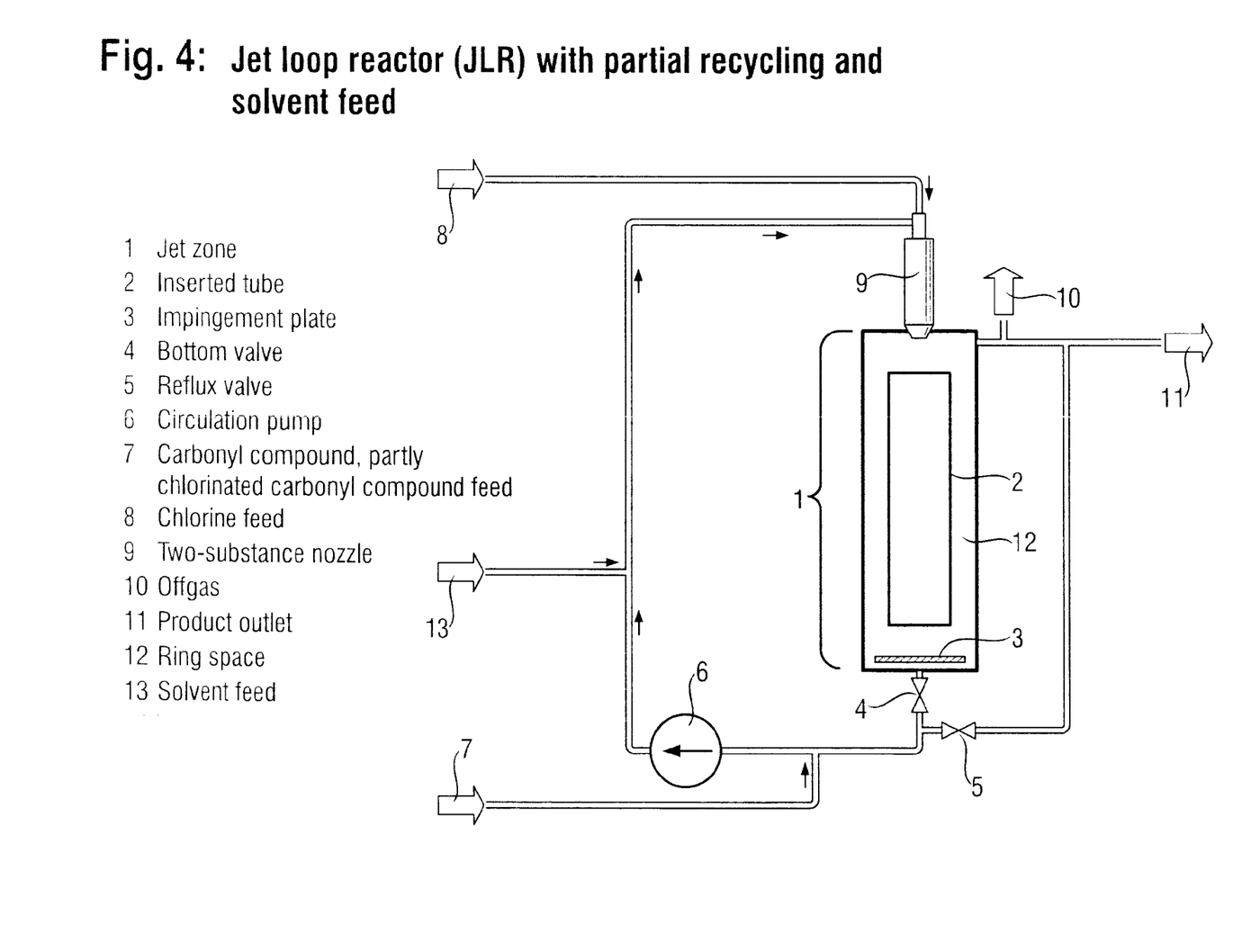
FIG. 4 shows a jet loop reactor (JZR) with partial recycling and solvent feed.

Continuous chlorination of propionaldehyde in dichloromethane with sulfuryl chloride to 2-chloropropionaldehyde in the jet loop reactor with partial recycling (see FIG. 4).

The selectivity for 2-chloropropionaldehyde is defined as follows:

$$Se(CPA) = \frac{CPA}{CPA + DCPA}$$

CPA=2-chloropropionaldehyde
DCPA=2,2-Dichloropropionaldehyde

| | |
|---|---|
| Temperature: | 25° C. |
| Pressure: | Standard pressure |
| SOCl2 mass flow: | 450-500 [kg/h] |
| Propionaldehyde mass flow: | 200-220 [kg/h] |
| Dichloromethane mass flow: | 200-220 [kg/h] |
| Reaction time: | 10 h |
| Conversion (GC): | 99% |
| Selectivity after 10 h: | 98% CPA |

Procedure:

Dichloromethane is initially charged in the reaction system via feed 13. By virtue of the opening of the bottom valve 4 and starting the circulation pump 6, a free jet through the two-substance nozzle 9 is generated. Propionaldehyde via feed 7 and sulfuryl chloride via feed 8 are introduced continuously through the two-substance nozzle 9. At the same time, dichloromethane as a solvent is metered continuously into the reactor via feed 13. The temperature is kept constant at 25° C. by means of an external circulation cooler. The finished product is obtained continuously via the outlet 12. The conversion and the selectivity are monitored by gas chromatography. As a result of the selectivity achieved, it is possible to dispense with a subsequent fractional purifying distillation. For product isolation, dichloromethane as the solvent is distilled off.

EXAMPLE 7

Figure 3:
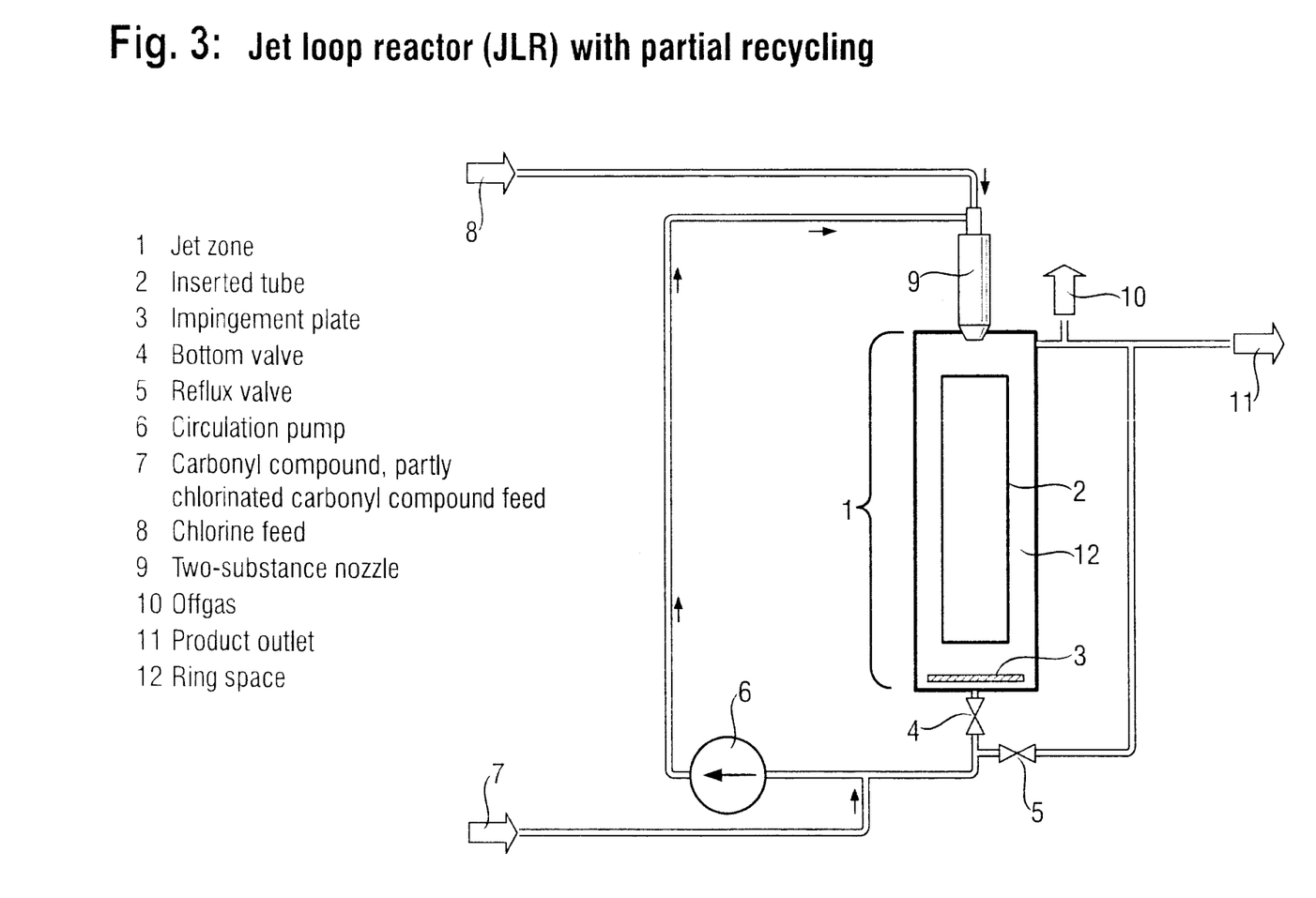
FIG. 3 shows a jet loop reactor (JLR) with partial recycling.

Semicontinuous chlorination of acetylacetone in a jet loop reactor with thionyl chloride to give 3-chloroacetylacetone, with partial recycling (see FIG. 3).

The selectivity for 3-chloroacetylacetone is defined as follows:

$$Se(3ClAcAc) = \frac{3ClAcAc}{3ClAcAc + 3,3ClAcAc}$$

3ClAcAc=3-chloroacetylacetone
3,3ClAcAc=3,3-dichloroacetylacetone

| | |
|---|---|
| Temperature: | 20° C. |
| Pressure: | Standard pressure |
| Thionyl chloride mass flow: | 30-40 [kg/h] |
| Reaction time: | 5 h |
| Amount used: | 160 kg of acetylacetone |
| Conversion after 5 h (GC): | 99% |
| Selectivity after 5 h: | 98% 3-chloroacetylacetone |

Procedure:

Acetylacetone is initially charged in the reaction system via feed 7. By virtue of the opening of the bottom valve 4 and starting the circulation pump 6, a free jet through the two-substance nozzle 9 is generated. Acetylacetone via feed 7 and thionyl chloride via feed 8 are introduced continuously through the two-substance nozzle 9. The temperature is kept at a constant 20° C. by means of an external circulation cooler. The conversion and selectivity are monitored by gas chromatography. As a result of the selectivity achieved, it is possible to dispense with a subsequent purifying distillation.

EXAMPLE 8

Figure 5:
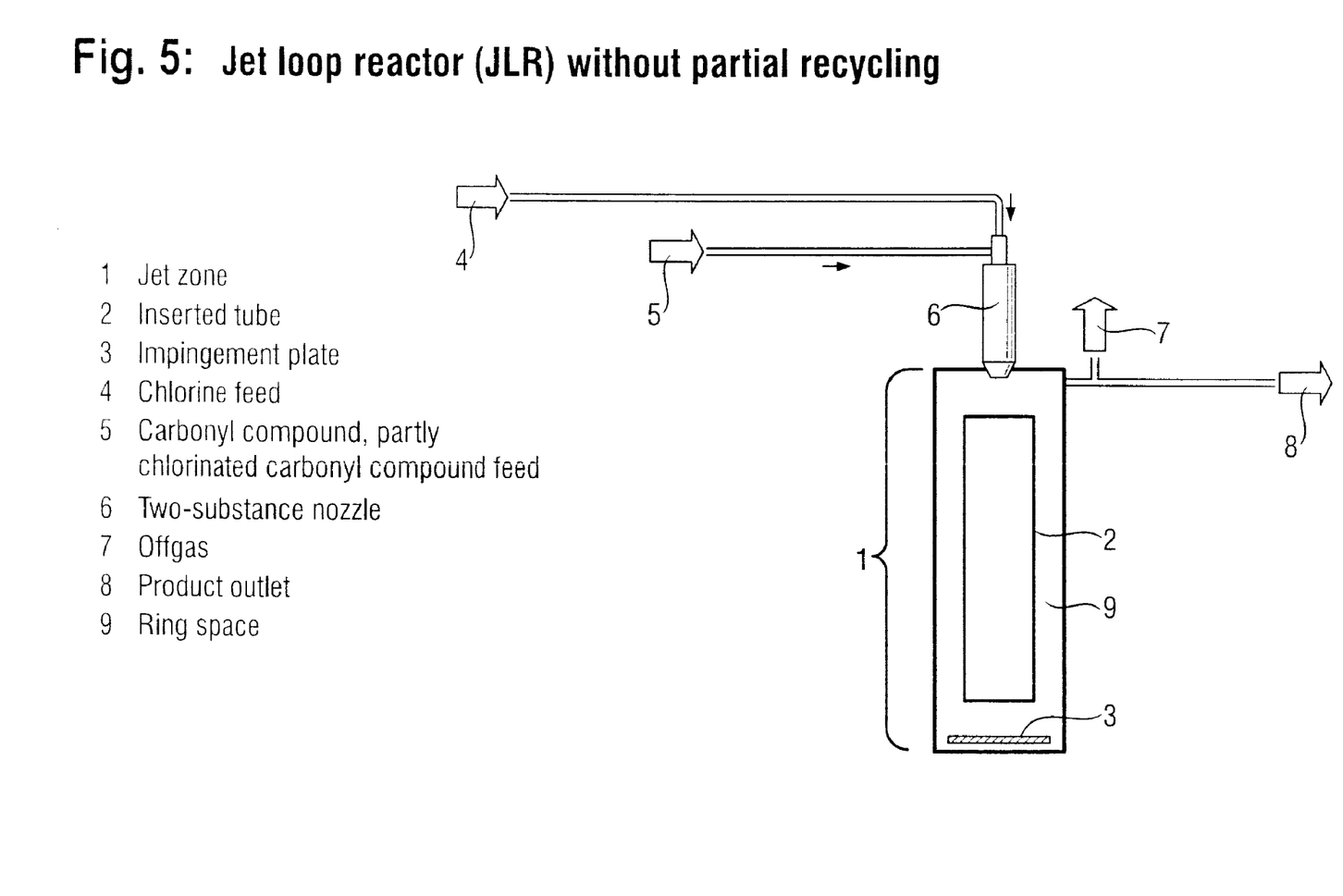
FIG. 5 shows a jet loop reactor (JLR) without partial recycling.

Continuous chlorination of cyclopentanone with chlorine to 2 chlorocyclopentanone in a jet loop reactor without partial recycling (see FIG. 5).

The selectivity for 2-chlorocyclopentanone is defined as follows:

$$Se(CPA) = \frac{CCPA}{CCPA + 2CCPE + 3CCPE}$$

CCPA=2-chlorocyclopentanone
2CCPE=3-chlorocyclopentene-1-one
3CCPE=3-chlorocyclopentene-1-one

| | |
|---|---|
| Temperature: | 20° C. |
| Pressure: | Standard pressure |
| Chlorine volume flow: | 40-45 [m$^3$ (STP)/h] |
| Cyclopentanone mass flow: | 1800-2000 [kg/h] |
| Reaction time | 12 h |

| | |
|---|---|
| Conversion (GC) | 10% |
| Selectivity after 10 h: | 99% CCPA |

Procedure:

Cyclopentanone via feed 5 and chlorine via feed 4 are introduced continuously through the two-substance nozzle 6. The temperature is kept at 25° C. by means of the jacket cooling of the jet loop reactor. The finished product is obtained continuously via the outlet 8. The conversion and the selectivity are monitored by gas chromatography. The excess cyclopentanone is separated continuously from the reaction product in a subsequent distillation and recycled to the chlorination.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A process for preparing chlorinated or partly chlorinated carbonyl compounds, comprising reacting unchlorinated or partly chlorinated carbonyl compounds with a chlorinating agent in a jet loop reactor.

2. The process of claim 1, wherein a jet zone loop reactor is used.

3. The process of claim 1, wherein the chlorinating agent is one or more chlorinating agents selected from the group consisting of chlorine, sulfuryl chloride and thionyl chloride.

4. The process of claim 2, wherein the chlorinating agent is one or more chlorinating agents selected from the group consisting of chlorine, sulfuryl chloride and thionyl chloride.

5. The process of claim 1, wherein the unchlorinated or partly chlorinated carbonyl compounds are straight-chain, branched, or have a cyclic structure.

6. The process of claim 1, wherein the chlorinating agent is metered into the unchlorinated or partly chlorinated carbonyl compound in the reactor in a volume flow ratio of from 1:1 to 1:4000.

7. The process of claim 1, wherein the unchlorinated or partly chlorinated carbonyl compounds are used neat or in the presence of one or more solvents.

8. The process of claim 1, wherein the reaction in the jet loop reactor takes place at a temperature of from 20° C. to 160° C.

9. The process of claim 1, wherein the reaction is performed in the presence of a catalyst.

10. The process of claim 1, wherein the reaction takes place in a continuous or semicontinuous mode.

11. The process of claim 1, wherein the continuous addition of chlorine comprises recycling of unconverted chlorine into the circuit.

12. The process of claim 1, wherein the chlorination is effected both with and without partial recycling.

13. The process of claim 1, wherein the chlorinating agent is chlorine.

14. The process of claim 1, which is uncatalyzed.

15. The process of claim 13, which is uncatalyzed.

16. The process of claim 1, wherein the carbonyl compound is a 1,3-dicarbonyl compound.

17. The process of claim 13 wherein the carbonyl compound is a 1,3-dicarbonyl compound.

18. The process of claim 14 wherein the carbonyl compound is a 1,3-dicarbonyl compound.

19. The process of claim 1, wherein the carbonyl compound is a ketone, an aldehyde, an acetoacetate ester, an acetoacetamide, or a malonate ester.

20. The process of claim 19, wherein the chlorinating agent is chlorine, and the reaction is uncatalyzed.

* * * * *